United States Patent
Nassopoulos

(10) Patent No.: US 9,795,501 B2
(45) Date of Patent: Oct. 24, 2017

(54) OSTOMY APPLIANCE REMOVABLE WASHABLE REUSABLE NON-ADHESIVE SEALING MEMBER

(71) Applicant: Achilles Nassopoulos, Montreal (CA)

(72) Inventor: Achilles Nassopoulos, Montreal (CA)

(73) Assignee: Achilles Nassopoulos, Notre Dame de l'Ile Perrot, QC ( * ) Notice: Subject to any disclaimer, the term of this patent is extended or adjusted under 35 U.S.C. 154(b) by 693 days.

(21) Appl. No.: 14/121,498

(22) Filed: Sep. 15, 2014

(65) Prior Publication Data

US 2016/0074206 A1  Mar. 17, 2016

(51) Int. Cl.
*A61F 5/445* (2006.01)
*A61F 5/449* (2006.01)

(52) U.S. Cl.
CPC ............. *A61F 5/445* (2013.01); *A61F 5/449* (2013.01)

(58) Field of Classification Search
CPC ............. A61F 5/448; A61F 2005/4486; A61F 2005/4483; A61F 5/449; A61F 5/443; A61F 5/445
USPC .................................. 604/338, 337, 339, 342
See application file for complete search history.

(56) References Cited

U.S. PATENT DOCUMENTS

| | | | | |
|---|---|---|---|---|
| 4,642,107 A * | 2/1987 | Arnone | .................... | A61F 5/448 604/342 |
| 4,883,477 A * | 11/1989 | Steer | ....................... | A61F 5/448 604/339 |
| 4,890,608 A * | 1/1990 | Steer | ....................... | A61F 5/443 602/52 |
| 4,973,323 A * | 11/1990 | Kaczmarek | ............. | A61F 5/448 604/277 |
| 5,785,695 A * | 7/1998 | Sato | ........................ | A61F 5/445 604/338 |
| 5,989,235 A * | 11/1999 | Quacquarella | .......... | A61F 5/445 604/332 |
| 6,537,261 B1 * | 3/2003 | Steer | ....................... | A61F 5/448 604/342 |

(Continued)

*Primary Examiner* — Matthew F Desanto

(57) ABSTRACT

An ostomy appliance consisting of an adhesive wafer (1) that permits exposing the skin (2) and Stoma (3) to the air and covering back repeatedly without removing the said adhesive wafer (1) from the said skin (2), comprising an annular adhesive wafer fabric membrane skirt (4) with a void (5), adhesive free interior, equipped with an annular male coupling (6) at the upper inner periphery of the said annular adhesive wafer fabric membrane skirt (4) to which a corresponding annular female coupling (7) fixed on the annular periphery of an annular impermeable barrier membrane (8) that has a central stoma size orifice (9) is coupled together, to which in turn an exact duplicate annular female coupling (10) as the said corresponding annular female coupling (7), equipped with a pouch (11) or other body waste or mucous collecting appliance, attaches together by way of piggyback or superimposition on top of the said corresponding annular female coupling (7). Two U-shaped plastic or metal spring clips (12) clamp and hold the said annular adhesive membrane skirt (4), the said annular impermeable barrier membrane (8), and the said pouch (11) or other body waste or mucous collecting appliance together. The couplings of the appliances of this patent can be reversed form male to female or vice-versa.

10 Claims, 9 Drawing Sheets

(56) References Cited

U.S. PATENT DOCUMENTS

| | | | | |
|---|---|---|---|---|
| 7,422,578 B2* | 9/2008 | Shan | ............... | A61F 5/448 604/332 |
| 7,867,207 B2* | 1/2011 | Therkelsen | ............ | A61F 5/448 403/202 |
| 2002/0032418 A1* | 3/2002 | Iseke | ............... | A61F 5/448 604/338 |
| 2002/0088080 A1* | 7/2002 | Fenton | ............... | A61F 5/445 15/389 |
| 2003/0004477 A1* | 1/2003 | Nielsen | ............... | A61F 5/443 604/336 |
| 2004/0073090 A1* | 4/2004 | Butler | ............... | A61B 17/0293 600/208 |
| 2009/0163886 A1* | 6/2009 | Therkelsen | ............ | A61F 5/448 604/342 |
| 2009/0299309 A1* | 12/2009 | Fenton | ............... | A61F 5/443 604/336 |
| 2011/0071485 A1* | 3/2011 | Foley | ............... | A61F 5/448 604/342 |
| 2012/0123363 A1* | 5/2012 | Grum-Schwensen | .. | A61F 5/448 604/342 |
| 2012/0165767 A1* | 6/2012 | Abrams | ............... | A61F 5/445 604/342 |
| 2012/0220967 A1* | 8/2012 | Lundholt | ............... | A61F 5/448 604/342 |
| 2013/0053803 A1* | 2/2013 | Willoughby | ............ | A61F 5/448 604/337 |
| 2014/0163495 A1* | 6/2014 | Nassopoulos | ........... | A61F 5/443 604/338 |
| 2014/0276519 A1* | 9/2014 | Luce | ............... | A61F 5/44 604/378 |
| 2014/0303541 A1* | 10/2014 | Vachon | ............ | A61F 13/00063 602/48 |
| 2014/0324002 A1* | 10/2014 | Luce | ............... | A61F 5/448 604/338 |

* cited by examiner

OSTOMY APPLIANCE REMOVABLE WASHABLE REUSABLE NON-ADHESIVE SEALING MEMBER

CROSS-REFERENCE TO RELATED APPLICATIONS

| Document Number Country Code- Number-Kind Code | Date MM-YYYY | Name | Classification |
|---|---|---|---|
| A) US.-6,210,384 B1 | 04-2001 | John B. Cline | 604/338 |
| B) US.-7,172,581 B2 | 02-2007 | Danuta Ciok Michael Hansen | 604/339 |
| C) US.-7,422,578 B2 | 09-2008 | Nicolas Shan Alexandre Macquin | 604/342 |
| D) US.-7,867,207 B2 | 01-2011 | Henning Therkelsen Holm Tina Soerensen Ole Madsboel Ingrid Fink | 604/342 |
| E) US.-8,684,982 B2 | 04-2014 | Tinh Nguyen-DeMary Mingliang Lawrence Tsai | 604/337 |
| F) US.-8,690,848 B2 | 04-2014 | Johnnie R. Cason | 604/342 |
| G) US.-8,764,717 B2 | 07-2014 | Alastair Willoughby Thomas Bates Jackson Gary Stacey | 604/337 |

BACKGROUND OF THE INVENTION

Colostomy is the surgical procedure of making an opening from the colon to the outside of the abdomen. In a colostomy, the surgeon may remove a segment of the colon, resulting in the colon being split into two separate parts. One end of the colon is passed through a small hole in the abdominal wall. This section of intestine called a stoma, allows for body waste to leave the body from the colon. The other end of the colon, which is attached to the rectum, may either be removed or closed off with sutures and left in the abdomen. There are other similar stoma operations such as ileostomy which is a stoma from the small intestine, and urostomy which is a stoma from the urinary system. Operations are performed for temporary or permanent stomas. Such operations are performed on humans and animals as well. In all cases, stoma wafers are used which are adhesive skin barriers or skin flanges with a fitted orifice at the center to allow the stoma to protrude. These stoma wafers consist of either a one piece wafer and bag or a two piece wafer with a snap-on or similar coupling for attaching the bag to the wafer. The bags are also known as pouches in the ostomy field. The bags clamp to a wafer by a coupling to retain the body waste discharged by the stoma. A major concern is the leaking of mucous and body wastes onto the skin surrounding the stoma. Generally ostomy wafers are produced with an orifice fitting as perfectly as possible around a stoma and held into position by adhesive. The adhesive generally covers the complete under surface of the ostomy wafer to secure against leakage for as long as the adhesive holds. The ostomy wafer is impermeable and must not lift around the stoma. The mucous and body waste irritate the skin around a stoma because of the low pH. Prolonged exposure of the low pH causes severe complications to the point of requiring surgery. All ostomy adhesive wafers invented and patented concentrate on leakage as the primary issue. Certain ostomy adhesive wafers have been invented with a central insert in the form of a removable Insert with a tacky adhesive backing in order to be able to remove it, wash it and reuse it, while still attaining the waterproof seal required until the adhesion is no longer sufficient to hold the appliance in place. Others have invented central inserts with specific shapes, in the form of a convex disc in order to try to improve the sealing efficiency. Such is the case with the following U.S. patents listed from A) to F).

A) Apr. 3, 2001, the U.S. patent U.S. Pat. No. 6,210,384 B1 that has a convex insert of a considerable thickness greater than 1/16 inch whereby the under surface of the wafer is totally covered with adhesive with the exception of the skin surface under the convex insert that contacts the skin around the stoma. The surface exposed without adhesive is less than 1/4 inch from the stoma. This surface is not sufficiently distanced from a stoma to prevent traumatizing the skin by adhesives and to prevent leaks due to the lifting of the wafer from lack of adhesion.

B) Feb. 6, 2007, the U.S. patent U.S. Pat. No. 7,172,581 B2 that is an adhesive wafer that has an insert in the form of a sealing disc that adheres by adhesion using adhesives. Therefore once again the under surface of the initial wafer and the insert cover the entire surface with adhesive, thus encountering the same complications of use and side effects as the U.S. patent U.S. Pat. No. 6,210,384 B1 described as item A) of this "Background of the invention" section of the present patent.

C) Sep. 9, 2008, the U.S. patent U.S. Pat. No. 7,422,578 B2 that has a fitted wafer with a coupling connecting the wafer to a detachable ostomy pouch. The wafer used again covers the entire under surface of the adhesive wafer that is in direct contact with the skin around a stoma.

D) Jan. 11, 2011, the U.S. Pat. No. 8,684,982 B2 that has several flangible bridges or annular shaped connections or adhesive type couplings attaching one to the other, however, once again the entire under surface of the appliance is covered with adhesive.

E) Apr. 8, 2014, the U.S. patent U.S. Pat. No. 8,690,848 B2 that has an elaborate ostomy closure for sealing an ostomy pouch consisting of an adhesive wafer with a plate orifice resembling the coupling wafer of the present invention, however, once again this apparatus has adhesive on the entire under surface of the initial layer that is exposed to the skin around a stoma.

F) Jul. 1, 2014, the U.S. patent U.S. Pat. No. 8,764,717 B2 that has an adhesive wafer with inner periphery surrounding the stoma of elastomeric material with a coupling to attach or receive a corresponding coupling ring arranged on an ostomy coupling bag.

In all the cases of inserts or center pieces described in the patents listed from A) to F) in the present patent "Background of the invention" section, adhesive substances cover the under surface of the wafers from 1/4 inch starting from the base of a stoma to the exterior periphery of the ostomy wafers. In other cases solid hard inserts thicker than 1/8 inch are inserted around a stoma. The key reason for keeping the adhesive wafers close to the base of a stoma is to cover the skin surface around a stoma with a waterproof impermeable substance that must be prevented from lifting. The key reason for solid hard inserts around a stoma is to try to create a better seal with specific shapes such as convex inserts around low profile or below the skin concave stomas.

The present invention is for an ostomy wafer appliance and method of securing around a stoma a thin central impermeable waterproof membrane, that is less than 1/16 inch thick with a central fitted stoma size orifice, which membrane is on an annular coupling that attaches and detaches by a coupling mechanism from an opposite corresponding male or female coupling on the inner upper periphery of an ostomy adhesive wafer fabric membrane skirt. An ostomy pouch or other body waste or mucous collecting appliance attaches by way of piggyback or superimposition onto the annular coupling with a similar opposite corresponding male or female coupling of the waterproof membrane and coupling assembly The appliance consists of an annular adhesive wafer fabric membrane skirt from inch to several inches wide with the center that is void. The said annular adhesive wafer fabric membrane skirt has adhesive on the complete undersurface. The said void is two (2) to four (4) times or more the diameter of the said stoma. The said annular adhesive wafer fabric membrane skirt is adhered to the skin around the said stoma by the said adhesive. The said annular adhesive wafer fabric membrane skirt has an annular coupling at the upper inner periphery of the said annular adhesive fabric membrane skirt. The said annular coupling is mechanically connected to an opposite corresponding male or female connecting annular coupling that is equipped with a sealing membrane on its inner annular periphery.

The said sealing membrane is less than 1/16 inch in thickness, is waterproof, pliable, malleable, has elastic properties and has a central orifice equal to or smaller than the stoma it is being applied to. The said sealing membrane covers the complete said void. The under surface of the said sealing membrane will not have adhesive. Instead, the under surface of the said sealing membrane will be void having nothing or there will be beneficial substitutes added as required such as fillers, gels, or creams.

The upper surface of the said opposite corresponding annular coupling is formed and shaped to mechanically superimpose and connect by way of piggyback or superimposition with an exact replica, duplicate, double of the said opposite corresponding annular coupling. The annular couplings will hold together mechanically by way of piggyback or superimposition at the upper surface of the said opposite corresponding annular coupling. The said exact replica of the said opposite corresponding annular coupling will be equipped with an ostomy pouch or other body waste or mucous collecting appliance that is attached at the inner periphery of the said exact replica annular coupling. The said exact replica annular coupling may also be used with a throw-away or a non-throw-away liner or pouch that is mechanically squeezed, clamped, in position between the said opposite corresponding annular coupling and the said exact replica of the said opposite corresponding annular coupling.

BRIEF SUMMARY OF THE INVENTION

It is the object of the present invention to create equipment and its corresponding method of use for fitting around an ostomy stoma a thin central impermeable waterproof membrane that has a surface with the diameter that is two (2) to four (4) times or more the diameter of the stoma, is less than 1/16 inch thick, has a central fitted stoma size orifice, has an annular coupling that attaches and detaches by a coupling mechanism from an opposite corresponding male or female annular coupling located at the inner upper periphery of an ostomy adhesive wafer fabric membrane skirt. An ostomy pouch or other body waste or mucous collecting appliance that is fixed to an annular coupling that is an identical replica, duplicate or double, of the annular coupling of the thin central impermeable waterproof membrane, attaches by way of piggyback or superimposition onto the top of the annular coupling on the central waterproof membrane.

The body waste or mucous collecting appliance is mechanically attached and detached from the central inner waterproof impermeable membrane at will and the central inner waterproof impermeable membrane is mechanically attached and detached from the adhesive wafer fabric membrane skirt at will thus exposing the bare stoma and an area with a diameter that is two (2) to four (4) times or more the diameter of the stoma.

With this invention:
1. An ostomy stoma can be exposed effortless for diagnosis, for treatment with a soothing cream or an antibiotic cream, for washing or for any other reason at any instance without traumatizing the skin around the stoma because of adhesives sticking to skin and hair.
2. The ostomy central waterproof impermeable membrane can be removed, washed and reused repeatedly.
3. The ostomy central waterproof impermeable membrane can be removed and the annular adhesive membrane skirt can be washed while adhering on the skin around a stoma.
4. The ostomy central waterproof impermeable membrane and the annular adhesive wafer membrane skirt can be removed, can be washed, and fresh adhesive can be applied on the under surface of the fabric of the annular adhesive wafer fabric membrane before fixing back on the skin around a stoma.
5. The ostomy wafers of this present invention will be far more ecological as far fewer numbers will be discarded because of the fact that all the parts are removable, washable, and reusable.
6. Ostomy rashes and infections will be considerably reduced thus reducing the load of help and care by medical professionals and related staff

DRAWINGS DETAILED EMBODIMENT

Figure 1:
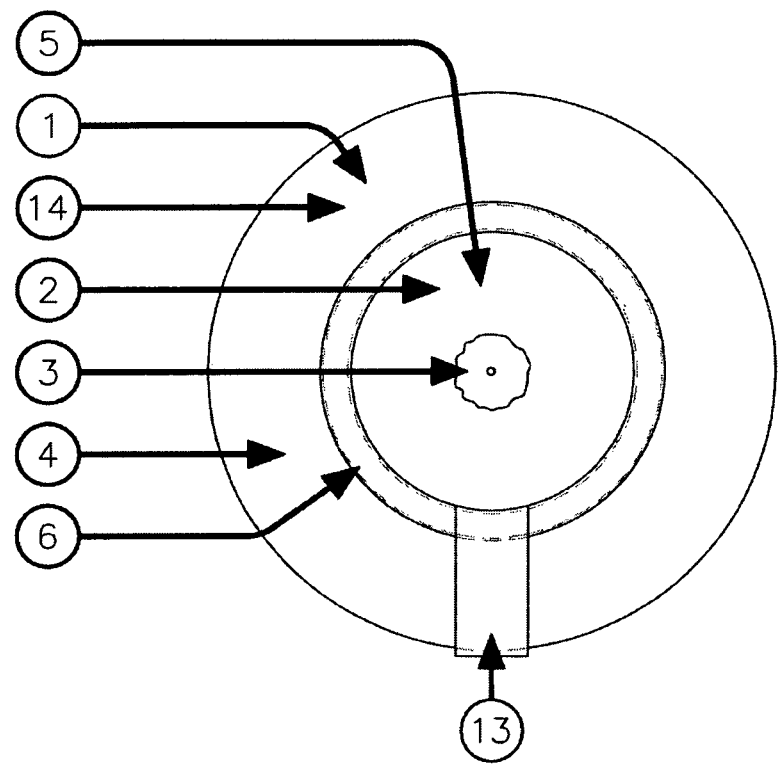
FIG. 1: Top surface view of annular adhesive wafer fabric membrane skirt on a stoma.
Figure 2:
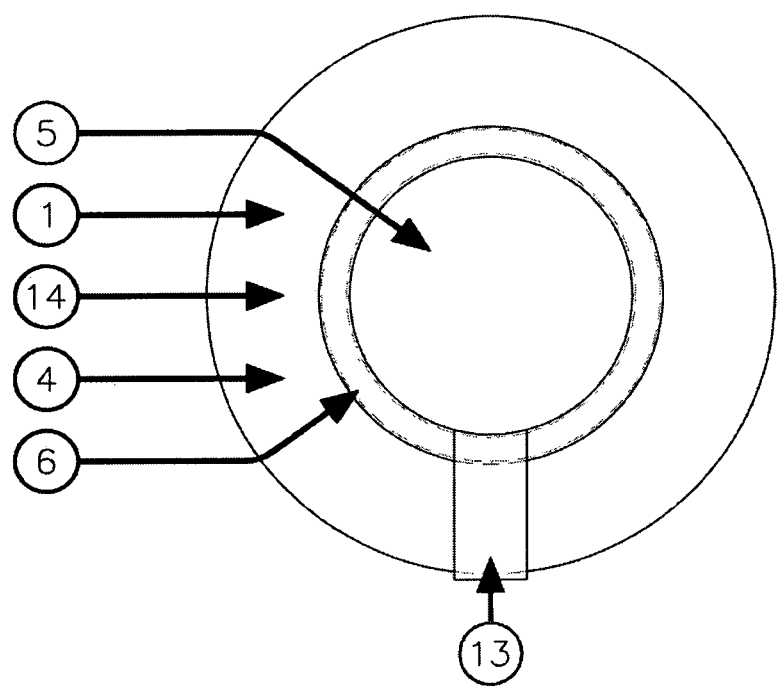
FIG. 2: Top surface view of annular adhesive wafer fabric membrane skirt.
Figure 3:
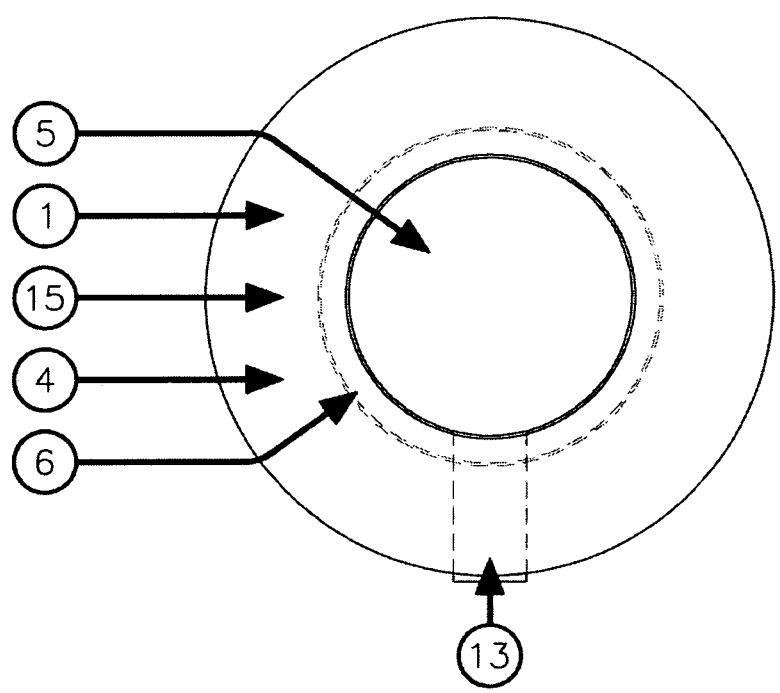
FIG. 3: Under surface view of annular adhesive wafer fabric membrane skirt.
Figure 4:
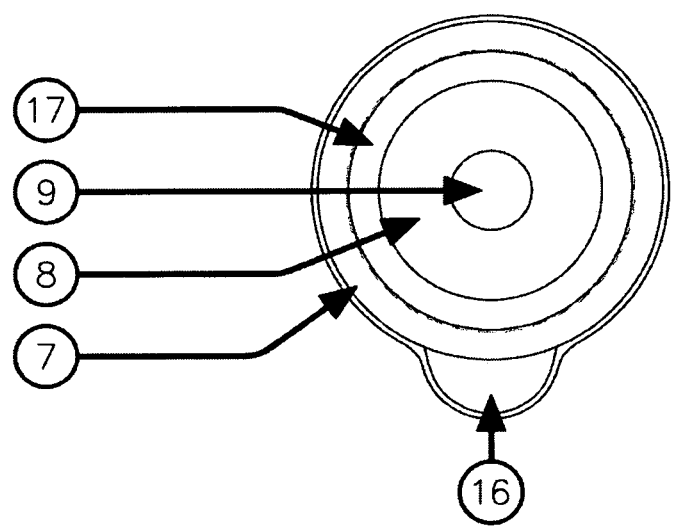
FIG. 4: Top surface view of corresponding annular female coupling with membrane assembly.
Figure 5:
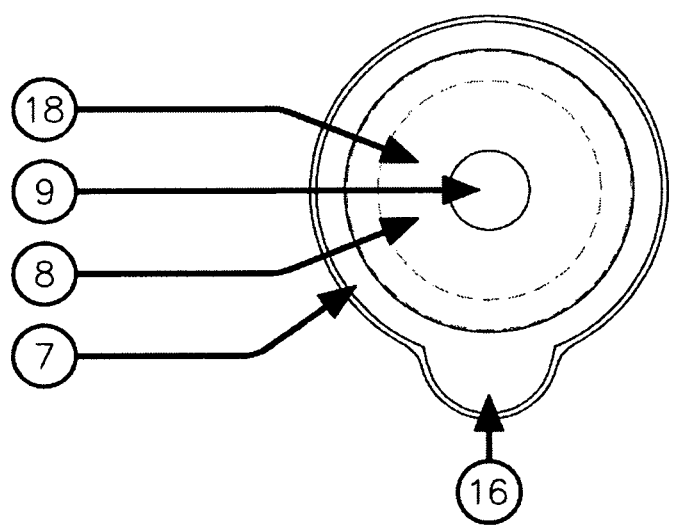
FIG. 5: Under surface view of corresponding annular female coupling membrane assembly.
Figure 6:
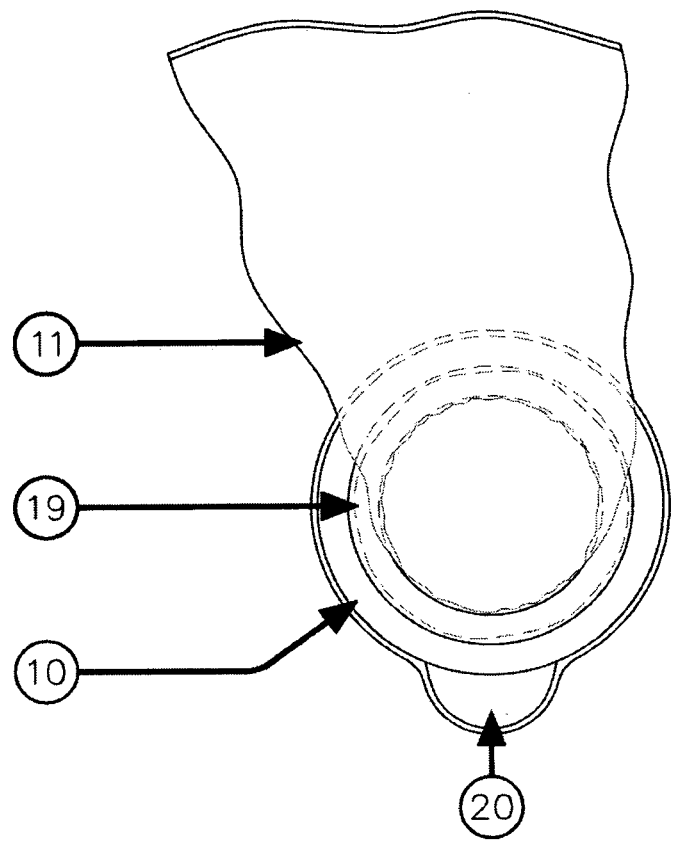
FIG. 6: Top surface view of exact duplicate annular female coupling with equipped with a pouch.
Figure 7:
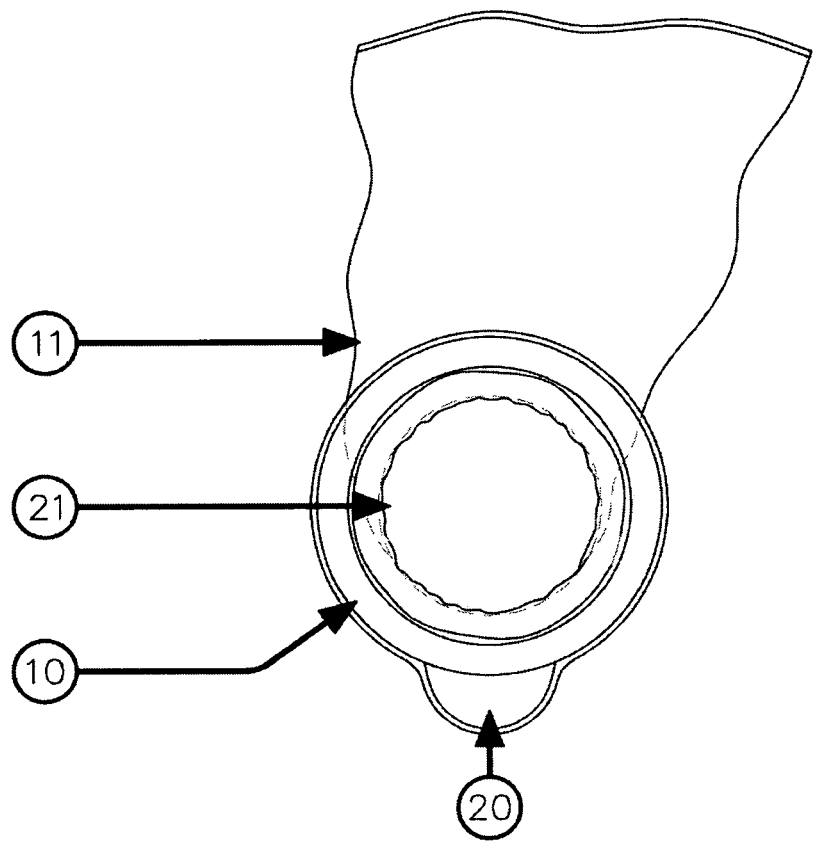
FIG. 7: Under surface view of exact duplicate annular female coupling equipped with a pouch.
Figure 8:
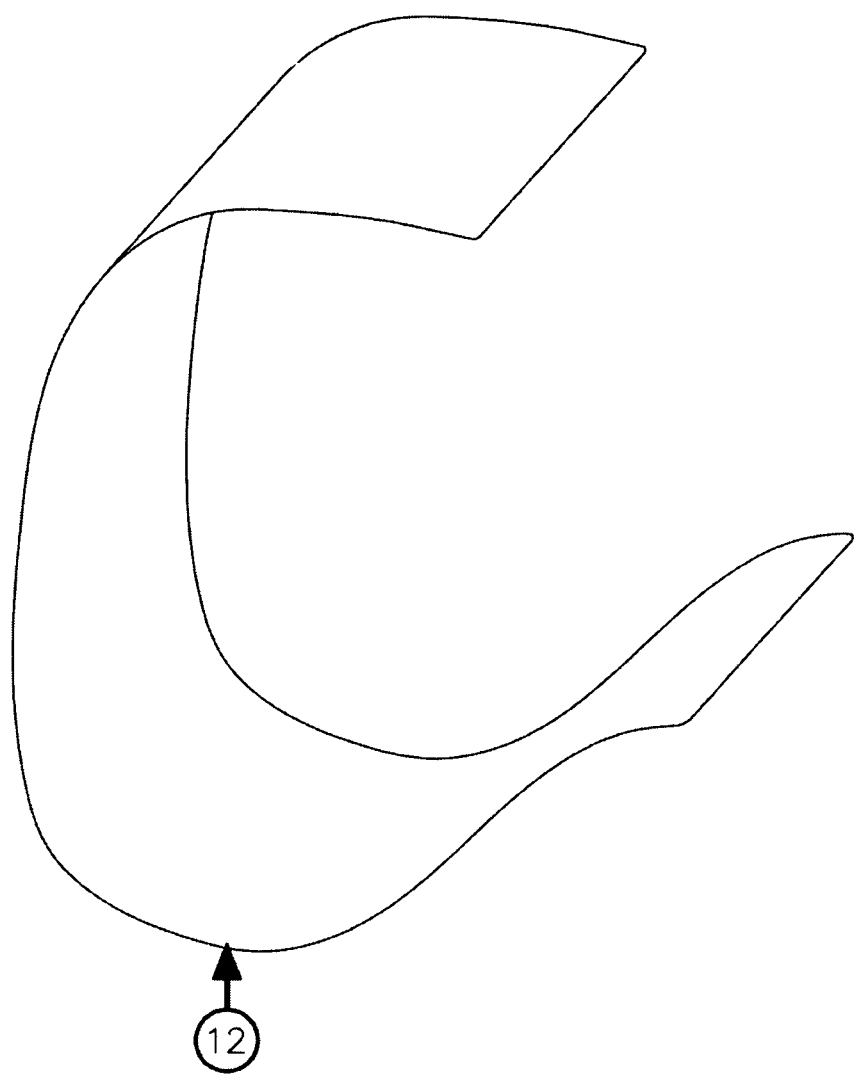
FIG. 8: U-shaped plastic or metal spring clips.
Figure 9:
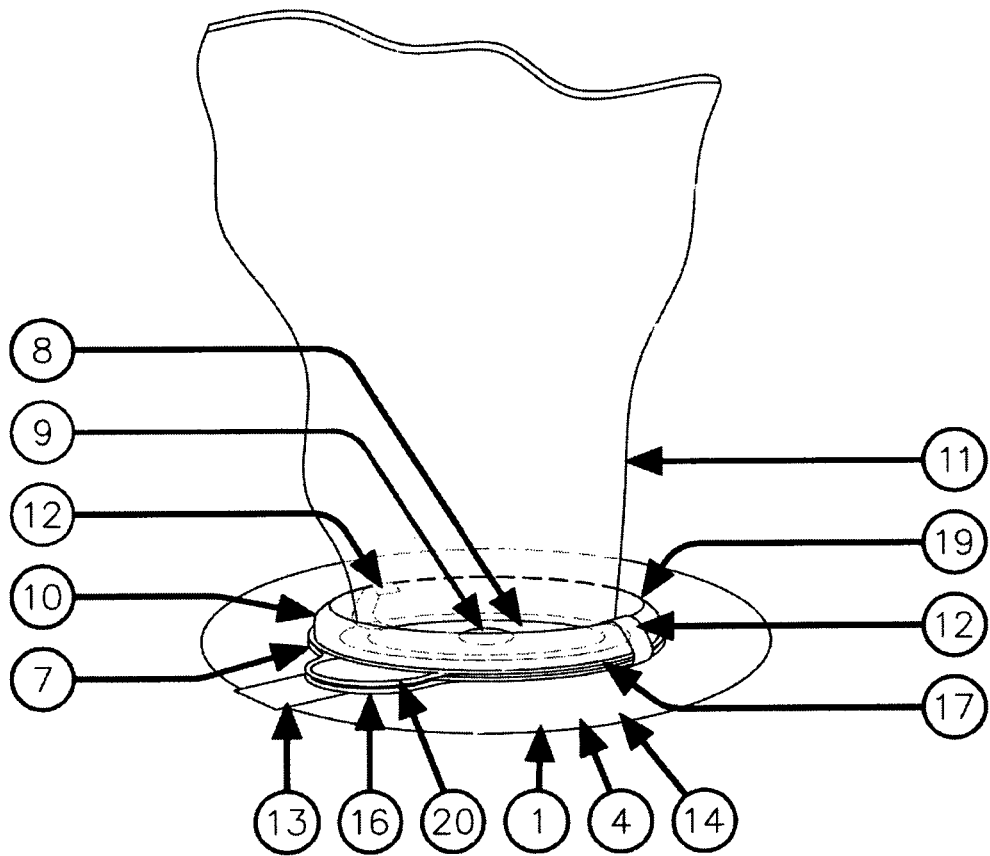
FIG. 9: Complete wafer assembly of the three (3) couplings assembled.

1) Adhesive wafer
2) Skin
3) Stoma
4) Annular adhesive wafer fabric membrane skirt
5) Void
6) Annular male coupling
7) Corresponding annular female coupling
8) Annular impermeable barrier membrane
9) Stoma size orifice
10) Exact duplicate annular female coupling
11) Pouch 12) U-shaped plastic or metal spring clip
13) Pulling tab
14) Top surface
15) Under surface
16) Pulling tab
17) Top surface
18) Under surface
19) Top surface
20) Pulling tab
21) Under surface

DETAILED DESCRIPTION OF THE INVENTION

The present invention is to facilitate the immediate examination and contact of the skin and stoma of an ostomy adhesive wafer in an area of skin from two (2) to four (4) times the diameter of the stoma it is being applied to without traumatizing the skin by adhesives. This is achieved by the following invention for an ostomy wafer appliance and method of securing around a stoma a thin central impermeable waterproof membrane, that is less than 1/16 inch thick with a central fitted stoma size orifice. This membrane is on an annular coupling that attaches and detaches by a coupling mechanism from an opposite corresponding male or female coupling on the inner upper periphery of an ostomy adhesive wafer fabric membrane skirt. An ostomy pouch or other body waste or mucous collecting appliance attaches by piggyback or by superimposition onto the annular coupling of the waterproof membrane and coupling assembly with a similar opposite corresponding male or female coupling.

The appliance consists of an annular adhesive wafer fabric membrane skirt that is from ½ inch to several inches wide with the center that is void. The said void is two (2) to four (4) times or more the diameter of the said stoma. The said annular adhesive wafer fabric membrane skirt is attached to the skin around the said stoma by adhesive. The said annular adhesive wafer fabric membrane skirt is equipped with an annular coupling at the upper inner periphery of the said annular adhesive fabric membrane skirt. The said annular coupling on the said annular adhesive wafer fabric membrane skirt is mechanically connected to an opposite corresponding male or female connecting annular coupling that is equipped with a sealing membrane on its inner annular periphery. The said sealing membrane is less than 1/16 inch in thickness, is waterproof, is pliable, is malleable, has elastic properties and has a central orifice equal to or smaller than the stoma it is being applied to. The said sealing membrane covers the complete said void. The under surface of the said sealing membrane will not have adhesive. Instead of adhesives the under surface of the said sealing membrane will be void or empty, or there will be beneficial substitutes added as required. Substitutes such as fillers or soothing or antimicrobial creams. Fillers will be in the form of gels that will remain in the gel form under the said sealing membrane forming a barrier to prevent being displaced by body wastes or mucous.

The upper surface of the said opposite corresponding annular coupling is formed and shaped to mechanically connect by way of piggyback or superimposition with an exact replica, double or twin, of the said opposite corresponding annular coupling and said sealing membrane assembly. The annular couplings will hold together mechanically by way of piggyback or superimposition at the upper surface of the said opposite corresponding annular coupling. The said exact replica of the said opposite corresponding annular coupling will be equipped with an ostomy pouch or other body waste or mucous collecting appliance that is permanently attached at the inner periphery of the said exact replica annular coupling. The said exact replica annular coupling may also be used with a throw-away or a non-throw-away liner or pouch that is mechanically squeezed, clamped, in position between the said opposite corresponding annular coupling and the said exact replica of the said opposite corresponding annular coupling.

The invention claimed is:

1. An ostomy appliance comprising;
   an annular adhesive wafer fabric membrane skirt with a void interior center, a top surface and an adhesive wafer configured to be placed on a skin surface, said annular fabric membrane skirt having an annular male coupling fixed at an upper inner periphery on said top surface;
   an annular thin impermeable barrier membrane with a central stoma size orifice, a first annular female coupling fixed on an annular periphery of said annular impermeable barrier membrane, wherein said annular impermeable barrier membrane is waterproof, pliable, malleable and has elastic properties;
   a pouch or other body waste collecting appliance attached to a top surface of a second female annular coupling;
   wherein said first and second annular female couplings are exact replicas and said first annular female coupling is configured to be attached to said annular male coupling and said second female coupling is configured to be attached to an upper surface of said first female coupling by way of piggyback or superimposition.

2. The ostomy appliance of claim 1 wherein the annular fabric membrane skirt is washable and reusable.

3. The ostomy appliance of claim 1 wherein a pulling tab from ¼ inch to 1 inch wide is fixed to the annular male coupling.

4. The ostomy appliance of claim 1 wherein the annular impermeable barrier membrane is 1/16 inch in thickness.

5. The ostomy appliance of claim 1 wherein the annular impermeable barrier membrane is removable, washable, and reusable.

6. The ostomy appliance of claim 1 wherein an adhesive is not applied to the void interior center.

7. The ostomy appliance of claim 1 wherein a filler in the form of a gel or cream is configured to be applied in the void interior center.

8. The ostomy appliance of claim 1, further includes a soothing or antimicrobial cream.

9. The ostomy appliance of claim 1, further including two u-shaped plastic or metal spring clips configured to hold the annular fabric membrane skirt, the annular impermeable barrier membrane and the pouch or other waste collecting appliance assembly together.

10. The ostomy appliance of claim 1 wherein said first and second annular female coupling each have a pulling tab from ¼ inch to 1 inch wide.

* * * * *